US007112702B2

(12) United States Patent
Carvill et al.

(10) Patent No.: US 7,112,702 B2
(45) Date of Patent: Sep. 26, 2006

(54) PROCESS FOR THE SYNTHESIS OF BISPHENOL

(75) Inventors: Brian Carvill, Evansville, IN (US); Katherine Glasgow, Evansville, IN (US); Gurram Kishan, Bangalore, IN (US); Ramesh Krishnamurti, Bangalore, IN (US); Nilesh Kumar Parkash Kukalyekar, Bangalore, IN (US); G. V. Ramanarayanan, Bangalore, IN (US)

(73) Assignee: General Electric Company, Schenectady, NY (US)

( * ) Notice: Subject to any disclaimer, the term of this patent is extended or adjusted under 35 U.S.C. 154(b) by 107 days.

(21) Appl. No.: 10/248,028

(22) Filed: Dec. 12, 2002

(65) Prior Publication Data

US 2004/0116751 A1 Jun. 17, 2004

(51) Int. Cl.
*C07C 39/16* (2006.01)
(52) U.S. Cl. ........................ 568/728; 528/196; 568/727
(58) Field of Classification Search ................ 568/727, 568/728; 528/196
See application file for complete search history.

(56) References Cited

U.S. PATENT DOCUMENTS

| 2,607,776 | A | 8/1952 | Vinton |
| 2,667,489 | A | 1/1954 | Fincke |
| 2,775,620 | A | 12/1956 | Williamson |
| 3,037,052 | A | 5/1962 | Bortnick |
| 3,049,568 | A | 8/1962 | Apel et al. |
| 3,153,001 | A | 10/1964 | Apel et al. |
| 3,172,916 | A | 3/1965 | Wagner |
| 3,198,847 | A | 8/1965 | Lanning |
| 3,242,219 | A | 3/1966 | Farnham |
| 3,367,979 | A | 2/1968 | Harper et al. |
| 3,394,089 | A | 7/1968 | McNutt et al. |
| 3,431,082 | A | 3/1969 | Sellin |
| 3,489,208 | A | 1/1970 | Manteufel |
| 3,535,879 | A | 10/1970 | Kuntz |
| 3,634,341 | A | 1/1972 | Gammill et al. |
| 3,651,080 | A | 3/1972 | Doebel et al. |
| 3,655,739 | A | 4/1972 | Clasen |
| 3,760,006 | A | 9/1973 | Gammill et al. |
| 4,036,974 | A | 7/1977 | Walker et al. |
| 4,045,379 | A | 8/1977 | Kwantes et al. |
| 4,051,079 | A | 9/1977 | Melby |
| 4,053,522 | A | 10/1977 | McClure et al. |
| 4,059,705 | A | 11/1977 | Walker |
| 4,122,048 | A | 10/1978 | Buchwalder et al. |
| 4,123,542 | A | 10/1978 | Walker |
| 4,126,618 | A | 11/1978 | Winter et al. |
| 4,177,350 | A | 12/1979 | Zirngibl et al. |
| 4,191,843 | A | 3/1980 | Kwantes et al. |
| 4,239,919 | A | 12/1980 | Hairston |
| 4,294,995 | A | 10/1981 | Faler et al. |
| 4,308,404 | A | 12/1981 | Kwantes et al. |
| 4,308,405 | A | 12/1981 | Kwantes |
| 4,315,023 | A | 2/1982 | Partyka et al. |
| 4,346,247 | A | 8/1982 | Faler et al. |
| 4,365,099 | A | 12/1982 | Faler et al. |
| 4,369,293 | A | 1/1983 | Heydenreich et al. |
| 4,391,997 | A | 7/1983 | Mendiratta |
| 4,396,728 | A | 8/1983 | Faler |
| 4,400,555 | A | 8/1983 | Mendiratta |
| 4,419,495 | A | 12/1983 | Davis |
| 4,423,252 | A | 12/1983 | Maki et al. |
| 4,424,283 | A | 1/1984 | Faler et al. |
| 4,439,545 | A | 3/1984 | Aspisi et al. |
| 4,448,899 | A | 5/1984 | Hass |
| 4,455,409 | A | 6/1984 | Faler et al. |
| 4,478,956 | A | 10/1984 | Maki et al. |
| 4,496,667 | A | 1/1985 | Reichgott et al. |
| 4,535,084 | A | 8/1985 | Lombardino et al. |
| 4,549,900 | A | 10/1985 | Kramer et al. |
| 4,579,857 | A | 4/1986 | Sherlock |
| 4,579,862 | A | 4/1986 | Manley et al. |
| 4,584,383 | A | 4/1986 | Parhi |
| 4,584,416 | A | 4/1986 | Pressman et al. |
| 4,590,303 | A | 5/1986 | Mendiratta |
| 4,595,704 | A | 6/1986 | Fazio |
| 4,675,458 | A | 6/1987 | Riemann et al. |
| 4,753,947 | A | 6/1988 | Dorn et al. |
| 4,758,573 | A | 7/1988 | Manley et al. |
| 4,789,745 | A | 12/1988 | Lin |
| 4,820,740 | A | 4/1989 | Li |
| 4,822,923 | A | 4/1989 | Li |
| 4,825,010 | A | 4/1989 | Li |
| 4,847,432 | A | 7/1989 | Faler |
| 4,859,803 | A | 8/1989 | Shaw |
| 4,895,905 | A | 1/1990 | Schneider et al. |
| 4,912,263 | A | 3/1990 | Rudolph et al. |
| 4,918,245 | A | 4/1990 | Iimuro et al. |
| 4,931,594 | A | 6/1990 | Knebel et al. |

(Continued)

FOREIGN PATENT DOCUMENTS

EP 0 552 518 1/1992

(Continued)

OTHER PUBLICATIONS

JP2003-231185. Publication Date Aug. 19, 2003. Abstract Only.

(Continued)

*Primary Examiner*—Michael L. Shippen

(57) ABSTRACT

A commercial scale continuous process for the production of a bisphenol comprising reacting a phenol and a ketone in the presence of a modified ion exchange resin catalyst, wherein said modified ion exchange resin comprises a crosslinked gellular acid functionalized polystyrene resin modified by neutralization of with a mercapto promoter.

80 Claims, No Drawings

U.S. PATENT DOCUMENTS

| | | | |
|---|---|---|---|
| 5,021,521 | A | 6/1991 | Krabbenhoft et al. |
| 5,036,073 | A | 7/1991 | Elbe et al. |
| 5,073,575 | A | 12/1991 | Blanch et al. |
| 5,075,511 | A | 12/1991 | Li |
| 5,087,767 | A | 2/1992 | Okamoto et al. |
| 5,100,460 | A | 3/1992 | Desbordes et al. |
| 5,141,966 | A | 8/1992 | Porath |
| 5,175,167 | A | 12/1992 | Zipperer et al. |
| 5,212,206 | A | 5/1993 | Rudolph et al. |
| 5,233,096 | A | 8/1993 | Lundquist |
| 5,284,981 | A | 2/1994 | Rudolph et al. |
| 5,296,609 | A | 3/1994 | McCort et al. |
| 5,302,774 | A | 4/1994 | Berg et al. |
| 5,304,688 | A | 4/1994 | Bowman et al. |
| 5,315,042 | A | 5/1994 | Cipullo et al. |
| 5,395,857 | A | 3/1995 | Berg et al. |
| 5,414,151 | A | 5/1995 | Pressman et al. |
| 5,414,152 | A | 5/1995 | Cipullo |
| 5,428,075 | A | 6/1995 | Pressman et al. |
| 5,436,344 | A | 7/1995 | Quallich |
| 5,455,282 | A | 10/1995 | Berg et al. |
| 5,463,140 | A | 10/1995 | Wehmeyer et al. |
| 5,475,154 | A | 12/1995 | Lundquist et al. |
| 5,545,764 | A | 8/1996 | Berg et al. |
| 5,589,517 | A | 12/1996 | Sugawara et al. |
| 5,608,071 | A | 3/1997 | Quallich |
| 5,629,456 | A | 5/1997 | Yamada et al. |
| 5,631,338 | A | 5/1997 | Inoue et al. |
| 5,648,561 | A * | 7/1997 | Tan et al. ................... 568/727 |
| 5,698,600 | A | 12/1997 | Wulff et al. |
| 5,700,943 | A | 12/1997 | Daines |
| 5,723,689 | A | 3/1998 | Pressman et al. |
| 5,723,691 | A | 3/1998 | Cipullo et al. |
| 5,756,781 | A | 5/1998 | Sybert et al. |
| 5,759,942 | A | 6/1998 | Tan et al. |
| 5,777,180 | A | 7/1998 | June et al. |
| 5,780,690 | A | 7/1998 | Berg et al. |
| 5,783,733 | A | 7/1998 | Kissinger |
| 5,785,823 | A | 7/1998 | Meurer et al. |
| 5,786,373 | A | 7/1998 | Hartman et al. |
| 5,789,628 | A | 8/1998 | Auer et al. |
| 5,914,431 | A | 6/1999 | Fennhoff |
| 5,929,249 | A | 7/1999 | Hill et al. |
| 5,932,731 | A | 8/1999 | Goda et al. |
| 5,939,494 | A | 8/1999 | Wehmeyer et al. |
| 5,973,103 | A | 10/1999 | Silva et al. |
| 6,020,385 | A | 2/2000 | Halle et al. |
| 6,013,845 | A | 3/2000 | Allan et al. |
| 6,114,539 | A | 9/2000 | Jautelat et al. |
| 6,133,190 | A | 10/2000 | Wehmeyer et al. |
| 6,133,486 | A | 10/2000 | Maas et al. |
| 6,211,417 | B1 | 4/2001 | Fengler et al. |
| 6,229,037 | B1 | 5/2001 | Okubo et al. |
| 6,265,409 | B1 | 7/2001 | Cheshire et al. |
| 6,288,284 | B1 | 9/2001 | Eek et al. |
| 6,329,556 | B1 | 12/2001 | Sakura et al. |
| 6,414,200 | B1 | 7/2002 | Spivack et al. |
| 6,534,686 | B1 | 3/2003 | Webb et al. |
| 2002/0123656 | A1 | 9/2002 | Spivack |
| 2003/0088130 | A1 | 5/2003 | Webb et al. |
| 2003/0153792 | A1 | 8/2003 | Iwahara et al. |
| 2004/0019242 | A1 | 1/2004 | Webb et al. |
| 2004/0030196 | A1 | 2/2004 | Saruwatari et al. |

FOREIGN PATENT DOCUMENTS

| | | |
|---|---|---|
| EP | 1 237 834 B1 | 10/2000 |
| EP | 1 371 623 A1 | 2/2002 |
| WO | WO 97/08122 | 3/1997 |
| WO | WO 00/23408 | 4/2000 |
| WO | WO 00/50372 | 8/2000 |
| WO | WO 00/61532 | 10/2000 |
| WO | WO 01/74488 | 3/2001 |
| WO | WO 01/74489 | 3/2001 |
| WO | WO 01/34544 | 5/2001 |
| WO | WO 01/49640 | 7/2001 |
| WO | WO 01/74750 | 10/2001 |
| WO | WO 02/070443 | 9/2002 |
| WO | WO 02/072516 | 9/2002 |
| WO | WO 02/085830 | 10/2002 |
| WO | WO 03/014049 | 2/2003 |
| WO | WO 03/055601 A1 | 7/2003 |

OTHER PUBLICATIONS

JP2003-226661. Publication Date Aug. 12, 2003. Abstract Only.
JP2001054034. Publication Date Feb. 23, 2001. Abstract Only (1 page).
JP 2001118012. Publication Date Apr. 27, 2001. Abstract Only (1 page).
FR 2685221. Publication No. Jun. 25, 1993. Abstract Only (1 page).
FR 2685323. Publication No. Jun. 25, 1993. Abstract Only (1 page).
DE 3619450. Publication Date. Dec. 16, 1987. Abstract Only (1 page).
EP 0676237. Publication Date. Oct. 11, 1995. Abstract Only (1 page).
EP1160229. Publication Date Dec. 5, 2001. Abstract Only (1 page).
EP 0788839. Publication Date Aug. 13, 1997. Abstract Only (1 page).
EP 0620041. Publication Date. Oct. 19, 1994. Abstract Only (1 page).
JP 2000143565. Publication Date. May 23, 2000. Abstract Only (1 page).
JP 2000281608. Publication Date Oct. 10, 2000. Abstract and Claims (6 pages).
JP 11255748 Publication Date. Sep. 21, 1999. Abstract Only (1 page).
JP 2001317768. Publication Date. Nov. 16, 2001. Abstract Only (1 page).
JP 2001021604. Publication Date Jan. 26, 2001 Abstract Only (1 page).
JP 2001054034. Publication Date. Feb. 23, 2001. Abstract Only (1 page).
JP 2001056471. Publication Date. Feb. 27, 2001. Abstract Only (1 page).
JP 2001064669. Publication Date. Mar. 13, 2001. Abstract Only (1 page).
JP 2001060201. Publication Date. Mar. 6, 2001. Abstract Only (1 page).
JP 2001064671. Publication Date. Dec. 17, 2002. Abstract Only (1 page).
JP 05-294875. Publication Date. Nov. 9, 1993 Abstract and Claims (5 pages).
JP 10-218814. Publication Date. Aug. 18, 1998. Abstract and Claims (6 pages).
JP 11-246458. Publication Date. Sep. 14, 1999. Abstract Only (3 pages).
JP 99179210 Machine Translation (1999) (13 pages).
JP 99255748 Machine Translation (1999) (9 pages).
JP 2002226417. Publication Date Aug. 14, 2002 Abstract Only (1 page).
JP 2001-286770. Publication Date Oct. 16, 2001. Abstract and Claims (5 pages).
JP 08-071433. Publication Date Mar. 19, 1996. Abstract and Claims (5 pages).
JP 10314595. Publication Date Dec. 2, 1998. Abstract and Claims (2 pages).
JP 10328573. Publication Date Dec. 15, 1998. Abstract and Claims (2 pages).
JP 10211434. Publication Date Aug. 11, 1998. Abstract and Claims (2 pages).
JP 5271132. Publication Date Oct. 19, 1993. Abstract and Claims (8 pages).

JP 8325185. Publication Date Dec. 10, 1996. Abstract and Claims (6 pages).
JP 11124351. Publication Date May 11, 1999. Abstract and Claims (9 pages).
JP 8038910. Publication Date Feb. 13, 1996. Abstract and Claims (5 pages).
JP 5294876. Publication Date Nov. 9, 1993. Abstract and Claims (4 pages).

JP2003246760. Publication Date. Sep. 2, 2003. Method for Producing Bisphenol A. (Abstract Only).
JP11179210. Publication Date: Jul. 6, 1999. Ion Exchange Resin and Preparation of Bisphenols Using Same as Catalyst. Abstract Only.
International Search Report mailed on Apr. 21, 2004.

* cited by examiner

PROCESS FOR THE SYNTHESIS OF BISPHENOL

BACKGROUND OF INVENTION

The disclosure relates to methods of making bisphenol employing an acidic ion exchange resin. In particular, the disclosure relates to methods of making bisphenol employing an acidic ion exchange resin and a promoter.

Typical bisphenols, such as 4,4'-isopropylidenediphenol, e.g., bisphenol-A (BPA), are widely employed as monomers in the manufacture of polymeric materials, such as engineering thermoplastics. For example, BPA is a principal monomer used in the manufacture of polycarbonate. Bisphenols are generally prepared by the electrophilic addition of aldehydes or ketones such as acetone to aromatic hydroxy compounds such as phenol, in the presence of an acidic catalyst composition. These types of reactions are also referred to as acid catalyzed condensation reactions. Commercially sulfonated polystyrene resin cross-linked with divinylbenzene, (PS-DVB) is typically used as the solid acid component of the catalyst composition. Reaction promoters can also be employed as part of the catalyst composition to improve the reaction rate, and selectivity, of the desired condensation reaction; in the case of BPA, the desired selectivity is for the para-para isomer. Promoters can be present as unattached molecules in the bulk reaction matrix, e.g., "bulk-promoters", or can be attached to the resin through ionic or covalent linkages, e.g., "attached-promoters". A useful class of promoter is the mercaptans, specifically thiols, e.g., organosulfur compounds which are derivatives of hydrogen sulfide.

There has been much published with regard to the use of bulk and attached promoters but much of the previous work has been related to small scale reactions that are typically performed in a batchwise fashion. There can be significant technical difficulty in applying attached promoters to large, commercial scale reactions, especially large scale reactions run in a continuous fashion.

SUMMARY OF INVENTION

The above-described and other drawbacks and disadvantages of the prior art are alleviated by a commercial scale continuous process for the reaction of a ketone with a phenol to form a bisphenol comprising reacting a feed comprising a phenol and a ketone at a phenol to ketone mole ratio of about 4 to about 65 by passing the feed at a weight hour space velocity of about 0.1 to about 10 through a modified ion exchange resin catalyst at an initial temperature of about 30 to about 100° C. to produce an effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

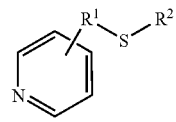

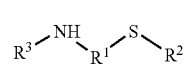

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing, and further wherein the effluent has a temperature about 4 to about 40° C. greater than the initial temperature.

In another embodiment, a process for the manufacture of polycarbonate comprises synthesizing a bisphenol by reacting a feed comprising a phenol and a ketone at a phenol to ketone mole ratio of about 4 to about 65 by passing the feed at a weight hour space velocity of about 0.1 to about 10 through a modified ion exchange resin catalyst at an initial temperature of about 30 to about 100° C. to produce effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

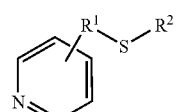

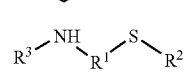

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing; and further wherein the effluent has a temperature about 4 to about 40° C. greater than the initial temperature; and reacting said bisphenol with a carbonic acid derivative or a carbonate diester in the presence of a polymerization catalyst.

In another embodiment, a commercial scale continuous process for the reaction of a ketone with a phenol to form a bisphenol comprises reacting a feed comprising a phenol and a ketone at a phenol to ketone mole ratio of about 4 to about 65 by passing the feed at a weight hour space velocity of about 0.1 to about 10 through at least 150 kilograms of a modified ion exchange resin catalyst at a temperature of about 30 to about 100° C., wherein the ketone comprises less than 250 parts per million methanol and the modified ion exchange resin catalyst comprises a crosslinked gellular acid functionalized polystyrene resin having acid sites and a premodification acidic milliequivalent per gram catalyst (meq/g) value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

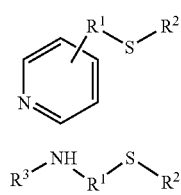

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing.

In another embodiment, a process for the manufacture of polycarbonate comprises synthesizing a bisphenol by reacting a feed comprising a phenol and a ketone at a phenol to ketone mole ratio of about 4 to about 65 by passing the feed at a weight hour space velocity of about 0.1 to about 10 through at least 150 kilograms of a modified ion exchange resin catalyst at a temperature of about 30 to about 100° C., wherein the ketone comprises less than 250 parts per million methanol and the modified ion exchange resin catalyst comprises a crosslinked gellular acid functionalized polystyrene resin having acid sites and a premodification acidic milliequivalent per gram catalyst (meq/g) value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

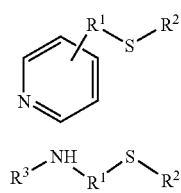

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing; and reacting said bisphenol with a carbonic acid derivative or a carbonic diester in the presence of a polymerization catalyst.

In another embodiment, a commercial scale continuous process for the reaction of a ketone with a phenol to form a bisphenol comprises reacting a feed comprising a phenol a ketone at a phenol to ketone ratio of about 4 to about 65 by passing the feed at a weight hour space velocity of about 0.1 to about 10 through a modified ion exchange resin catalyst at an initial temperature of about 30 to about 100° C. to produce an effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst (meq/g) value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is a promoter compound having the formula

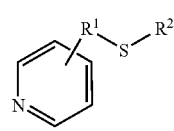

wherein $R^1$ is an alkylene having 1 to about 10 carbons and $R^2$ is a hydrogen, t-butyl or acyl and further wherein the effluent has a temperature about 4 to about 40° C. greater than the initial temperature.

In another embodiment, an effluent from a commercial scale continuous reaction of a ketone with a phenol to form a bisphenol comprises phenol, para-para and ortho-para bisphenol wherein the para-para: ortho-para ratio is greater than about 40.0, the amount of para-para bisphenol is greater than or equal to about 93% by weight, based on the total weight of the effluent minus the weight of phenol and the total amount of bisphenol is greater than or equal to about 10% by weight, based on the total weight of the effluent.

DETAILED DESCRIPTION

A commercial scale continuous process for the production of bisphenol comprises reacting a phenol and a ketone by passing a feed comprising the phenol and ketone through a modified ion exchange resin catalyst. Commercial scale processes can be characterized by the use of greater than about 150 kilograms of modified ion exchange catalyst, by the change in temperature over the course of the reaction due to a scale of the exothermic reaction or by both the amount of modified ion exchange resin catalyst and the change in temperature. The modified ion exchange resin catalyst comprises a crosslinked gellular acid functionalized polystyrene resin having acid sites and a premodification acidic milliequivalent per gram catalyst (meq/g) value greater than or equal to about 3.5 meq/gram when dry. The resin is modified by neutralizing about 35 to about 75 mole % of the resin acid sites with a mercapto promoter selected from the group consisting of promoter compounds I and II having the formula

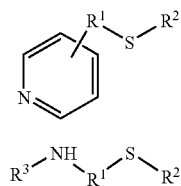

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing.

The continuous process has high selectivity for para-para (p/p) bisphenol and a high conversion level, thereby significantly reducing the complexity of the large scale isolation processes required to obtain the isolated bisphenol. The average p/p selectivity of the commercial scale continuous process is greater than or equal to about 93%, preferably greater than or equal to about 95%, and more preferably greater than or equal to about 97%. Average p/p selectivity is determined by 100×(amount of p/p bisphenol created in the reactor/total amount of products created in the reactor).

The commercial scale continuous process is capable of achieving initial conversion levels greater than or equal to about 90%, preferably greater than or equal to about 95% and more preferably greater than or equal to about 97% As readily appreciated by one of ordinary skill in the art, conversion will decrease over the lifetime of the catalyst. It is contemplated that when the conversion level of the catalyst has decreased to about 80% the catalyst will be replaced or reactivated using methods known in the art such as those found in U.S. Pat. Nos. 5,428,075 and 5,455,282. Conversion is defined herein as 100×((ketone into reaction–ketone out of reaction)/ketone into reaction). Conversion has a theoretical maximum of 100%.

The high p/p selectivity and high initial conversion level of the large scale continuous process is dramatic and unexpected. The effectiveness of a catalyst, as determined by selectivity and conversion, can vary dramatically based on the sheer size of the reaction. Without being bound by theory it is believed differences in selectivity and conversion may be due to a difference in reaction conditions of large scale reaction compared to small scale reactions. For example, large scale commercial reactions typically exhibit a significant increase in reaction temperature as the flow proceeds from inlet to outlet, in part due to the exothermic nature of the reaction. Small scale reactions typically exhibit little or no temperature increase form inlet to outlet. A small scale reaction employing a catalyst, such as one done on a milligram scale, may demonstrate excellent selectivity and conversion but when the reaction conditions are scaled up to a multi-gram or kilogram scale the selectivity can decrease. Thus, not all catalysts employing attached promoters that exhibit good selectivity and conversion on a small scale are useful or economical on a commercial scale.

Similarly, the selectivity achieved in a batch process is not necessarily predictive and may not correlate with the selectivity achieved in a continuous process due to significant differences in reaction conditions such as reactant concentration over the course of the reaction. Use of the above described promoters to form a modified ion exchange catalyst for use in a continuous commercial scale reaction results in a reaction having high conversion and excellent selectivity for p/p bisphenol.

High catalyst selectivity in the reactor is desired in order to simplify downstream separation operations and to maximize raw material yields. Many catalysts that are used commercially do not exhibit very high selectivity if the feed comprises only phenol and ketone. In this case, the net selectivity can be improved by recycling impurities to the reactor to suppress isomerization reactions and/or further production of impurities. These impurities are typically recycled from the product stream of a previous alkylation reaction (pass). The disadvantage of this scheme is that the purity of the effluent stream is lowered by the presence of the recycled impurities. One unexpected result for the catalysts described herein is that they can achieve high selectivity even in the absence of recycle. This enables simpler downstream isolation schemes because the purity of bisphenol in the reactor effluent is higher. Catalysts which exhibit high selectivities under conditions which use substantial levels of impurity recycle to the reactor would be expected to exhibit lower selectivities under virgin feed (substantially no impurity recycle) conditions.

In another aspect, the modified ion exchange resin catalyst demonstrates a total bisphenol selectivity (para-para (p/p) and ortho-para (o/p) combined) of greater than or equal to about 98.5%. Additionally, the average p/p:o/p ratio is greater than or equal to about 20, preferably greater than or equal to about 30 and more preferably greater than or equal to about 40. The high overall selectivity when combined with the high p/p o/p ratio indicates that little or no impurity aside from o/p bisphenol is produced. It is contemplated that the high overall selectivity increases the life of the catalyst.

Phenol starting materials are any aromatic hydroxy compounds which have at least one unsubstituted position, and optionally have one or more inert substituents such as hydrocarbyl or halogen at one or more ring positions. An inert substituent is a substituent which does not interfere undesirably with the condensation of the phenol and ketone or aldehyde and which is not, itself, catalytic. Preferably, the phenols are unsubstituted in the position para to the hydroxyl group.

Alkylene, alkyl, cycloaliphatic, aryl, arylene, alkylarylene, arylalkylene, alkylcycloaliphatic and alkylenecycloaliphatic are hydrocarbyl functions, that is, functions containing carbon and hydrogen atoms. The alkylene functions can be straight or branched chain and saturated or unsaturated, that is alkylene, alkenylene, or alkynylene. Cycloaliphatic hydrocarbon residues include both saturated and unsaturated cyclic residues, that is, cycloalkylene and cycloalkenylene. Arylene includes mono- and polycyclic aromatic residues, e.g. those of benzene, biphenyl, biaryl, naphthyl, phenanthrenyl, anthracenyl or aryl groups, including those bridged by an alkylene group. Alkaryl residues include alkyl, alkenyl and alkynyl-substituted aromatic rings. Aralkyl includes alkyl, alkenyl or alkynyl residues, substituted by one or more aromatic groups.

Alkyl groups include both straight- and branched-chain isomers of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, nonadecyl and eicosyl groups, as well as the corresponding unsaturated (alkenyl or alkynyl) groups, as well as higher homologues. Preferably, the alkyl groups are of 1–20 carbon atoms, more preferably of 1–5 carbon atoms, most preferably those of 1–3 carbon atoms. Alkyl of 1–5 carbon atoms includes the various methyl, ethyl, propyl, butyl and pentyl isomers. Alkyl, aryl, alkaryl and aralkyl substituents are suitable hydrocarbyl substituents on the phenol reactant.

Other inert substituents on the phenols include, but are not limited to alkoxy, aryloxy or alkaryloxy, wherein alkoxy includes methoxy, ethoxy, propyloxy, butoxy, pentoxy, hexoxy, heptoxy, octyloxy, nonyloxy, decyloxy and polyoxyethylene, as well as higher homologues; aryloxy, phenoxy, biphenoxy, naphthyloxy, etc. and alkaryloxy includes alkyl, alkenyl and alkylnyl-substituted phenolics.

Additional inert substituents on phenols include halo, such as bromo, chloro or iodo.

Cyano and nitro substituents may deactivate the phenols and aldehyde and carboxylic acid substituents may cause interfering reactions. Additional hydroxyl substituents may be suitable in some cases.

Preferred substituents include alkyl moieties containing from 1 to about 10 carbon atoms, more preferably, lower alkyl moieties, containing from 1 to about 5 carbon atoms, most preferably from 1 to 3 carbon atoms. The alkyl substituents may be straight or branched chain isomers.

Exemplary phenols include, but are not limited to, phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tertbutylphenol, 2-phenylphenol, 1-naphthol, 2-naphthol and the like. Preferred phenols include phenol, 2- or 3-cresol, 2,6-dimethylphenol, resorcinol, naphthols, and mixtures thereof. Most preferably, the phenol is unsubstituted.

The phenol starting materials may be commercial grade or better. As readily understood by one of ordinary skill in the art commercial grade reagents may contain measurable levels of typical impurities such as acetone, α-methylstyrene, acetophenone, alkyl benzenes, cumene, cresols, water, hydroxyacetone, methyl benzofuran, methyl cyclopentenone, and mesityl oxide, among others.

The ketones, which are advantageously used, include any ketone having a single carbonyl (C=O) group or several carbonyl groups, and which are reactive under the conditions used. The ketones can be substituted with substituents that are inert under the conditions used. Inert substituents are as set forth above for the reactive phenols.

The ketones are advantageously selected from aliphatic, aromatic, alicyclic or mixed aromatic-aliphatic ketones, diketones or polyketones, of which acetone, methyl ethyl ketone, diethyl ketone, benzyl, acetyl acetone, methyl isopropyl ketone, methyl isobutyl ketone, acetophenone, ethyl phenyl ketone, cyclohexanone, cyclopentanone, benzophenone, fluorenone, indanone, 3,3,5-trimethylcyclohexanone, anthraquinone, 4-hydroxyacetophenone, acenaphthenequinone, quinone, benzoylacetone and diacetyl are representative examples.

Ketones having halo, nitrile or nitro substituents can also be used, for example, 1,3-dichloroacetone or hexafluoroacetone.

Aliphatic ketones which are useful starting materials include, but are not limited to acetone, ethyl methyl ketone, isobutyl methyl ketone, 1,3-dichloroacetone, hexafluoroacetone and the like. A preferred aliphatic ketone is acetone, which condenses with phenol to produce 2,2-bis-(4-hydroxyphenyl)-propane, commonly known as bisphenol A. Another preferred aliphatic ketone is hexafluoroacetone, which reacts with two moles of phenol to produce 2,2-bis-(4-hydroxyphenyl)-hexafluoropropane (bisphenol AF).

A preferred class of ketones has at least one hydrocarbyl group containing an aryl group, for example, a phenyl, tolyl, naphthyl, xylyl or 4-hydroxyphenyl group.

Other preferred ketones include those in which the hydrocarbon radicals connected to the carbonyl groups of the ketone is in a cycloaliphatic group. Examples of specific preferred ketones include 9-fluorenone, cyclohexanone, 3,3,5-trimethylcyclohexanone, indanone, indenone, anthraquinone and the like.

Most preferred ketones include 9-fluorenone, benzophenone, acetone, acetophenone, 4-hydroxyacetophenone, 4,4'-dihydroxybenzophenone and mixtures of the foregoing ketones. Most preferably, the process of this invention is used to make bisphenol A by reaction of phenol with acetone or to make 9,9-bis-(4-hydroxyphenyl)fluorene (BHPF) by reaction of phenol with 9-fluorenone.

The ketone starting materials may be commercial grade or better. As readily understood by one of ordinary skill in the art commercial grade reagents may contain measurable levels of typical impurities such as aldehydes, acetophenone, benzene, cumene, diacetone alcohol, water, mesityl oxide, and methanol, among others. When the ketone used is acetone it preferably contains less than about 250 ppm of methanol.

The disclosed process can also be used for the condensation of phenols with aldehydes, for example, with formaldehyde, acetaldehyde, propionaidehyde, butyraldehyde or higher homologues of the formula RCHO, wherein R is alkyl of 1–20 carbon atoms. The condensation of two moles of phenol with one mole of formaldehyde produces bis-(4-hydroxyphenyl)methane, also known as Bisphenol F.

It will be understood that dialdehydes and ketoaldehdyes, for example, glyoxal, phenylglyoxal or pyruvic aldehyde, can also be used.

The products are generally geminal bisphenols, that is, compounds having one or more single carbon atoms to which are attached nuclei of two phenolic moieties. This single carbon atom corresponds to the carbonyl carbon of the ketone or aldehyde reactant. In the case of starting materials, containing more than one aldehyde or ketone carbonyl, the product will contain more than one geminal bisphenolic moiety. For example, the condensate from acetyl acetone and phenol is 2,2,4,4-tetrakis-(hydroxyphenyl)pentane and the condensate from benzoylacetone is 2,2,4,4-tetrakis-(hydroxyphenyl)-4-phenylbutane.

The ion exchange resin comprises a cross-linked polystyrene resin that is functionalized to have acid sites. The polystyrene resin may be cross-linked with a variety of known cross-linker such as polycyclic aromatic divinyl monomers, divinyl benzene, divinyl toluene, divinyl biphenyl monomers and combinations of the foregoing cross-linkers. Preferably the polystyrene resin is cross-linked with divinylbenzene. The acid sites may comprise a sulfonic acid functionality, which upon deprotonation produces a sulfonate anion functionality, a phosphonic acid functionality, which upon deprotonation produces a phosphonate anion functionality, or a carboxylic acid functionality, which upon deprotonation produces a carboxylate anion functionality. The degree of crosslinking is typically greater than or equal to about 1%, preferably greater than or equal to about 1.5%, and more preferably greater than or equal to about 2%. Alternatively, the degree of crosslinking is less than or equal to about 8%, preferably less than or equal to about 6%, and more preferably less than or equal to about 4%. The ion exchange resin may comprises a mixture of resins with different degrees of crosslinking wherein the degree of crosslinking of each resin is as defined above.

The ion exchange resin may be a monodispersed resin, polydispersed resin, or a combination of the foregoing.

The ion exchange resin has an acidic milliequivalent per gram catalyst value (proton exchange capacity), prior to modification, of greater than or equal to about 3.5, preferably greater than or equal to about 4, and more preferably greater than or equal to about 5 meq/g when dry.

Exemplary ion exchange resin include, but are not limited to, Diaion® SK104, Diaion® SK1B, Diaion® PK208, Diaion® PK212 and Diaion® PK216 (manufactured by Mitsubishi Chemical Industries, Limited), A-121, A-232, and A-131, (manufactured by Rohm & Haas), T-38, T-66 and T-3825 (manufactured by Thermax), Lewatit K1131, Lewatit K1221 (manufactured by Bayer), Dowex® 50W2X, Dowex® 50W4X, Dowex 50W8X resins (manufactured by Dow Chemical), Indion 180, Indion 225 (manufactured by Ion Exchange India Limited), and Purolite CT-222 and Purolite CT-122 (manufactured by Purolite).

Promoter compound I is represented by the formula:

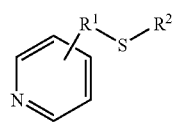

(I)

wherein $R^1$ is an alkene having 1 to about 10 carbons and $R^2$ is hydrogen, t-butyl or acyl. Preferably $R^1$ is ethylene and $R^2$ is hydrogen. As readily understood by one of ordinary skill in the art, the term pyridyl describes a six membered aromatic ring containing five carbon atoms and one nitrogen atom. The mercaptan substituent ($-R^1-S-R^2$) may be located at the 2-, 3- or 4-position on the ring with the 2- and 4-positions preferred and the 4-position especially preferred. The promoter may be added to the ion exchange resin as a salt or other precursor form that readily converts to the promoter under the conditions for neutralization.

Promoter compound II represented by the formula:

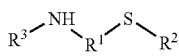

(II)

wherein $R^1$ and $R^2$ are defined as above. $R^3$ is hydrogen, $C_1$ to $C_5$ carboxylate or a branched, unbranched or cyclic alkyl group having 1 to about 10 carbons. Preferably $R^1$ is ethylene, $R^2$ is hydrogen and $R^3$ is hydrogen. The promoter may be added to the ion exchange resin as a salt or other precursor form that readily converts to the promoter under the conditions for neutralization. Exemplary precursor forms for cysteamine ($R^1$ is ethylene, $R^2$ is hydrogen and $R^3$ is hydrogen) are cysteamine HCl and 2,2'-dimethylthiazolidine.

The promoter is typically fixed to an ion exchange resin support. Generally the ion exchange resin is modified by neutralizing resin acid sites with a promoter or combination of promoters to form a modified ion exchange resin catalyst. In an exemplary process, the promoter(s) is combined with water to form an aqueous mixture. The aqueous mixture may further comprise an acid to improve solubility of the promoter(s). The amount of acid is sufficient to solubilize the promoter but not enough to impede modification of the ion exchange resin. Useful amounts of acid are typically less than or equal to about 1 equivalent and preferably less than or equal to about 0.25 equivalents, based on the number of moles of the promoter(s). Exemplary acids include, but are not limited to, hydrochloric acid (HCl), p-toluenesulfonic acid, trifluorocacetic acid, and acetic acid. The aqueous mixture is contacted with the ion exchange resin resulting in an ionic linkage between the promoter cation and anion (deprotonated acid site) of the ion exchange resin. Formation of the ionic linkage neutralizes the acid site.

The degree of neutralization of the ion exchange resin is greater than or equal to about 35 mole %, preferably greater than or equal to about 40 mole %, based on the total moles of acid sites. The degree of neutralization is typically less than or equal to about 75 mole %, preferably less than or equal to about 60 mole %, more preferably less than or equal to about 55 mole %, and most preferably less than or equal to about 50 mole %, based on the total moles of acid sites. The neutralization (modification) of the ion exchange resin with a promoter reduces the number of catalytic acid sites. It is unexpected that an ion exchange resin with such a high number of neutralized catalytic sites as described herein would provide high conversion and high p/p and total selectivities.

The degree of neutralization may be determined in a number of ways. The modified ion exchange resin catalyst may be titrated to determine the amount of remaining acid sites, the —SH content can be determined by a suitable analytical method or the nitrogen content can be determined by a suitable analytical method. The results obtained with these analytical methods are consistent with each other.

Following modification (neutralization), the modified ion exchange resin catalyst is rinsed with a continuous flow of phenol to remove substantially all of the water. Alternatively, if acid was used to improve the solubility of the promoter, the modified ion exchange resin is rinsed with deionized water prior to rinsing with phenol. Removing substantially all of the water is herein defined as removing greater than or equal to about 75%, preferably greater than or equal to about 80%, more preferably greater than or equal to about 85%, based on the total amount of water initially employed. Preferably the phenol has been subjected to purification steps to remove metallic and organic impurities that may be present through the use of resin treatment as taught in U.S. Pat. No. 5,414,151 or other known purification methods.

Ketone or aldehyde is then added to the phenol flowing through the ion exchange resin to form the feed. The ketone or aldehyde contains less than or equal to about 250, preferably less than or equal to about 225, and more preferably less than or equal to about 200 parts per million (ppm) of methanol. Ketone is typically present in an amount sufficient to result in a phenol to ketone mole ratio greater than or equal to about 4, preferably greater than or equal to about 5, and more preferably by greater than or equal to about 7. The phenol to ketone mole ratio is typically less than or equal to about 65, preferably less than or equal to about 40, and more preferably less than or equal to about 15, based on the total weight of phenol. Ketone may be added to the phenol in a single portion (at a single location along the continuous flow through the modified ion exchange resin catalyst) or in multiple portions (multiple locations along the continuous flow through the modified ion exchange resin catalyst). Preferably the ketone is added in equal multiple portions, and most preferably in two or four equal portions along the course of the modified ion exchange resin catalyst.

The feed may also contain low levels of bisphenol and impurities resulting from the manufacture of bisphenol. As described below, it can be desirable to recycle residual phenol and other starting materials found in the effluent stream. The residual phenol and other starting materials are typically isolated before being recycled to the reaction feed but small amounts of impurities can remain and thus become part of the feed. Typically, the amount of bisphenol and other materials that are not reaction starting materials is less than about 2% by weight, based on the total weight of the feed and as determined by liquid chromatograph (LC) although it is contemplated that the amount of bisphenol and other non-reaction starting materials present in the feed may be in amounts as high as about 15% by weight, based on the total weight of the feed and as determined by liquid chromatograph (LC).

The feed comprising phenol and ketone is passed through the modified ion exchange resin catalyst at an overall weight hourly space velocity greater than or equal to about 0.1, preferably greater than or equal to about 0.5, and more preferably greater than or equal to about 0.6. The feed comprising phenol and ketone is typically passed through the modified ion exchange resin catalyst at an overall weight hourly space velocity less than or equal to about 10.0, preferably less than or equal to about 8.0, and more preferably less than or equal to about 3.0, and more preferably less than or equal to about 2.5.

The feed comprising phenol and ketone is introduced to the modified ion exchange resin catalyst at a temperature of about 10° C. to about 100° C. Within this range the introductory temperature is preferably greater than or equal to about 30° C., preferably greater than or equal to about 40° C., more preferably greater than or equal to about 45° C. Also within the above mentioned range, the temperature of the modified ion exchange resin catalyst at the introduction of the feed and is less than or equal to about 90° C., and preferably less than or equal to about 80° C.

In a commercial scale reactor the temperature of the vessel increases from inlet to outlet due to the exothermic nature of the reaction. Without being bound by theory, it is thought that the temperature increase from inlet to outlet gives rise to differences in catalyst performance on a lab scale (in which the small scale does not cause a discernable temperature rise) compared to a commercial scale, in which the temperature rise is both observable and affects the catalyst performance. The effluent comprising phenol, reaction products, water, and residual ketone exits from the modified ion exchange resin catalyst at a temperature about 4 to about 40° C. greater than the introductory temperature. Preferably the effluent temperature at exit is about 10 to about 30° C., and more preferably about 15 to about 25° C., greater than the introductory temperature.

Passing the feed through the modified ion exchange resin catalyst results in an effluent comprising bisphenol, residual starting materials, water produced in the reaction, and side products. The bisphenol produced (in the effluent) is predominantly para-para (p/p) bisphenol although some ortho-para (o/p) is produced. Typically the average ratio of p/p:o/p is greater than or equal to about 20, preferably greater than or equal to about 30 and more preferably greater than or equal to about 40 in the effluent stream. The effluent contains greater than or equal to about 93, preferably greater than or equal to about 95, and more preferably greater than or equal to about 96% by weight p/p bisphenol, based on the total weight of the effluent minus the weight of the phenol in the effluent. The effluent contains greater than or equal to about 10%, preferably greater than or equal to about 12%, and more preferably greater than or equal to about 15% by weight total bisphenol (o/p and p/p combined), based on the total weight of the effluent.

The bisphenol is then isolated from the residual starting materials, water and side products found in the effluent. In the isolation process, water, residual ketone and optionally some residual phenol are removed first, typically by vacuum distillation resulting in a bisphenol containing product stream. The removed ketone and residual phenol can be separated from the water and recycled to the reaction feed. The p/p bisphenol may be isolated from the bisphenol containing product stream by adduct crystallization, solvent crystallization, melt crystallization, distillation, or a combination of the foregoing isolation methods. If adduct crystallization is employed in combination with any of the other isolation methods, it is preferable for adduct crystallization to comprise the first step and the other isolation method(s) to comprise the subsequent step(s) of the chosen combination. The phenol removed from the product stream may be recycled for use in the catalyzed reaction or adduct crystallization when present. Advantageously, the high degree of selectivity of the reaction for p/p bisphenol results in the amount of impurities being greatly reduced, thus facilitating the isolation of the p/p bisphenol, improving the overall efficiency of the reaction and isolation, lengthening the life of the catalyst, as well as reducing the cost of the production of p/p bisphenol. The ability of this catalyst to be used with a virgin feed system, without significant recycle of impurities to the reactor, also results in a higher purity effluent, further simplifying or eliminating the purification process.

The bisphenol may be used in the synthesis of polycarbonate. Polycarbonate may be synthesized by interfacial polymerization methods or by transesterification methods. In interfacial polymerization, an aqueous solution of a bisphenol is combined with an organic solution containing an organic solvent and a carbonic acid derivative, such as carbonyl halides, diaryl carbonate esters and haloformates such as phosgene, in the presence of a polymerization catalyst. Polymerization occurs at the interface between two phases. Additionally a monofunctional compound such as a phenol, tert-butyl phenol or para-cumylphenol, may be present to function as a chain termination agent to limit the molecular weight of the polycarbonate. A polyfunctional compound, herein defined as having more than two functional groups, may also be present to function as a branching agent. An exemplary polyfunctional compound is tris-hydroxyphenolethane (THPE).

Useful organic solvents include, but are not limited to, aliphatic hydrocarbons, chlorinated aliphatic hydrocarbons, aromatic hydrocarbons, substituted aromatic hydrocarbons and carbon disulfide. The chlorinated aliphatic hydrocarbons, especially methylene chloride, are preferred.

Exemplary polymerization catalysts include tertiary amines, typically a trialkylamine such as triethylamine, highly nucleophilic heterocyclic amines such as 4-dimethylaminomorpholine, phase transfer catalysts such as quaternary ammonium salts and mixtures of the foregoing. Exemplary quaternary ammonium salts include tetra-t-butylammonium chloride or bromide and tetra-t-butylphosphonium chloride or bromide.

Transesterification may be performed with or without solvent. When performed without solvent the reaction is run at high temperature and low pressure and has come to be known as "melt polymerization." In transesterification, a carbonate diester is condensed with bisphenol in the presence of a polymerization catalyst such as the amines described above, guanidine, alkali metal phosphates, and alkali earth metal phosphates. The reaction mixture may further comprise a polyfunctional compound and/or a monofunctional compound as described above.

Useful carbonate diesters include, but are not limited to, diphenyl carbonate, bis (4-t-butylphenyl) carbonate, bis(2,4-dichlorophenyl) carbonate, bis methyl salicyl carbonate, bis(2,4,6-trichlorophenyl) carbonate, bis(2-cyanophenyl) carbonate, bis(o-nitrophenyl) carbonate, ditolyl carbonate, m-cresol carbonate, dinapthyl carbonate, bis(diphenyl) carbonate, diethyl carbonate, dimethyl carbonate, dibutyl carbonate, or dicylcohexyl carbonate. Of these, diphenyl carbonate is preferred. If two or more of these compounds is combined, it is preferable to use diphenyl carbonate as one component of the combination.

All cited patents are incorporated herein by reference in their entirety.

The invention is further illustrated by the following non-limiting examples.

EXAMPLES

The following examples employ the ion exchange resins shown in Table 1.

TABLE 1

| Tradename | Degree of crosslinking | Acidic meq value | Type of ion exchange resin | Manufacturer |
|---|---|---|---|---|
| Lewatit | 2% | ~5 meq/g | polydispersed | Bayer |
| T-3825* | 2% | ~5 meq/g | polydispersed | Thermax |
| T-3825* | 2.5% | ~5 meq/g | polydispersed | Thermax |
| T-66 | 8% | ~5 meq/g | polydispersed | Thermax |
| Indion 180 | 8% | ~5 meq/g | polydispersed | Indion |
| CT-222 | 2% | >5 meq/g | polydispersed | Purolite |
| CT-122 | 2% | 5 meq/g | polydispersed | Purolite |
| A131 | 4% | ~5 meq/g | monodisperse resin | Rohm & Haas |
| A121 | 2% | ~5 meq/g | monodisperse | Rohm & Haas |

*T-3825 is available with differing degrees of crosslinking

The promoters employed in the Examples are shown in Table 2.

TABLE 2

| Structure | Name |
|---|---|
| (pyridyl-CH2CH2-SH) | 4-pyridylethylmercaptan (PEM) |
| (NH2-CH2CH2-SH) | 2-aminoethanethiol (cysteamine) |

Neutralization procedure.

The ion exchange resin was combined with water to form an aqueous slurry which was acidified with para-toluenesulfonic acid. The solution was stirred and deaerated with flowing nitrogen gas for about 30 minutes. The promoter was then added and the resulting mixture was stirred for about 4 hours. The modified resin was then filtered and washed with water until the pH of the eluted wash water was equal to the pH of the water prior to washing. The resin was then dried and the acid milliequivalency (meq/g) value and neutralization level determined by titration. The relative amounts of resin and promoter determined the neutralization level.

Analytical procedures.

In order to assess the performance and characteristics of the catalysts, well-known analytical procedures were used. The acetone weight percent of the feed and effluent was determined by treatment of the sample with hydroxylamine hydrochloride, followed by titration of the liberated HCl. To measure the acid milliequivalency (meq/g) value, the resin was first dried to remove all water. A weighed amount of resin was treated with aqueous NaCl to liberate HCl, and the isolated HCl solution was titrated to determine moles of acid present and calculate a milliequivalents of acid/gram catalyst (meq/g) value. The conversion was then calculated as described previously. The weight percents of para-para bisphenol, ortho-para bisphenol, phenol, and bisphenol impurities were determined by standard high pressure liquid chromatography. The para-para bisphenol selectivity, overall bisphenol selectivity, and para-para bisphenol to ortho-para bisphenol ratio were then calculated, as previously described, using the observed weight percents.

Examples 1–84

Single Column

10–15 grams of the modified ion exchange resin catalyst was packed into a column and held in place by a combination of glass wool and sand. The column was surrounded by a water jacket maintained at a temperature of about 55–75° C. as indicated in Table 3. A feed mixture comprising phenol and about 4.8 weight percent acetone, as shown in Table 3, was added to the top of the column. Addition of the feed was controlled by a pump so as to maintain the weight hour space velocity indicated in Table 3. The effluent from the column was collected and analyzed by acetone titration, water titration and liquid chromatography. As can be seen by the results in Table 3 the small scale reactions show a trend of increasing selectivity with increased attachment level. Selectivity however, generally decreases with an increase in the scale of the reaction.

TABLE 3

| Ex. | Promoter | Resin | Degree of Neutralization | Acetone % | Temp (° C.) | WHSV | P/P selectivity | p/p:o/p ratio | Conversion | Overall bisphenol selectivity |
|---|---|---|---|---|---|---|---|---|---|---|
| 1 | PEM | T-66 | 16% | 4.8 | 65 | 1 | 96.91 | 59.0 | 93.7 | 98.55 |
| 2 | PEM | T-66 | 30% | 4.8 | 65 | 1 | 96.81 | 65.1 | 81.8 | 98.30 |
| 3 | PEM | A 121 | 40% | 4.8 | 65 | 1 | 96.23 | 41.2 | 97.1 | 98.57 |
| 4 | PEM | A 121 | 58% | 4.8 | 65 | 1 | 96.69 | 49.7 | 97.2 | 98.64 |
| 5 | PEM | T-66 | 16% | 4.8 | 65 | 2 | 97.00 | 61.2 | 88.6 | 98.58 |
| 6 | PEM | T-66 | 30% | 4.8 | 65 | 2 | 96.70 | 69.2 | 76.0 | 98.10 |
| 7 | PEM | A 121 | 33% | 4.8 | 65 | 2 | 96.36 | 44.3 | 95.2 | 98.54 |
| 8 | PEM | A 121 | 40% | 4.8 | 65 | 2 | 96.22 | 42.3 | 97.5 | 98.49 |
| 9 | PEM | A 121 | 48% | 4.8 | 65 | 2 | 96.29 | 43.3 | 97.5 | 98.52 |
| 10 | PEM | A 121 | 58% | 4.8 | 65 | 2 | 96.52 | 48.3 | 94.5 | 98.52 |
| 11 | PEM | T-66 | 16% | 4.8 | 75 | 1 | 96.18 | 41.9 | 98.5 | 98.47 |
| 12 | PEM | T-66 | 30% | 4.8 | 75 | 1 | 96.37 | 52.3 | 86.5 | 98.21 |
| 13 | PEM | A 121 | 40% | 4.8 | 75 | 1 | 94.72 | 26.2 | 99.1 | 98.34 |
| 14 | PEM | A 121 | 48% | 4.8 | 75 | 1 | 94.94 | 27.4 | 94.9 | 98.40 |
| 15 | PEM | A 121 | 58% | 4.8 | 75 | 1 | 95.66 | 34.3 | 99.6 | 98.45 |
| 16 | PEM | T-66 | 16% | 4.8 | 75 | 2 | 96.33 | 46.9 | 94.8 | 98.39 |
| 17 | PEM | T-66 | 30% | 4.8 | 75 | 2 | 96.29 | 55.0 | 80.4 | 98.04 |
| 18 | PEM | A 121 | 33% | 4.8 | 75 | 2 | 95.05 | 29.2 | 97.9 | 98.30 |
| 19 | PEM | A 121 | 40% | 4.8 | 75 | 2 | 95.39 | 32.2 | 98.9 | 98.35 |
| 20 | PEM | A 121 | 48% | 4.8 | 75 | 2 | 95.53 | 33.5 | 99.4 | 98.38 |
| 21 | PEM | A 121 | 58% | 4.8 | 75 | 2 | 96.06 | 40.7 | 96.6 | 98.42 |

Examples 22–26

Multiple Stage

Four column, each containing 10 grams of modified ion exchange catalyst were arranged in series. After the modified ion exchange resin was added to the columns the resin was flushed with phenol until the amount of water in the effluent was determined to be less than 1% by Karl Fisher titration. The columns were surrounded by water jackets maintained at a temperature of about 55° C. A total of 5 weight % acetone was added in four equal parts (four additions of about 1.25 weight %). Addition of the feed to each column was controlled by a pump so as to attain an overall space velocity of 1–2 WHSV. The effluent from the columns was collected and analyzed by acetone titration, water titration and liquid chromatography. Results are shown in Table 4.

columns was collected and analyzed by acetone titration, water titration and liquid chromatography. Initial conversion was 98%. The p/p:o/p ratio was 46.4. The p/p selectivity was 96.75%, and overall BPA selectivity was 98.84%.

As can be seen from the foregoing Examples, it is possible to produce bisphenol on a commercial scale using continuous process employing a modified ion exchange catalyst. Surprisingly, high degrees of neutralization of the ion exchange catalyst result in high levels of conversion and an average p/p bisphenol selectivity of greater than about 96%. Additionally, the average p/p:o/p ratio is greater than 20.0 and the total bisphenol selectivity is greater than 98.5%. The process produces substantially no impurities other than ortho-para bisphenol.

While the invention has been described with reference to a preferred embodiment, it will be understood by those skilled in the art that various changes may be made and

TABLE 4

| Example | Promoter | Resin | Degree of Neutralization | Acetone % | Number of Acetone stages | Temp (° C.) | p/p selectivity | p/p:o/p ratio | Conversion | Overall bisphenol selectivity |
|---|---|---|---|---|---|---|---|---|---|---|
| 22 | Cysteamine | Lewatit | 16 | 5 | 4 | 55 | 96.79 | 41.4 | 80.5 | 99.13 |
| 23 | Cysteamine | Lewatit | 26 | 5 | 4 | 55 | 96.84 | 44.1 | 77 | 99.04 |
| 24 | Cysteamine | Lewatit | 56 | 5 | 4 | 55 | 96.83 | 51.2 | 49 | 98.72 |
| 25 | PEM | A 121 | 33 | 5 | 4 | 55 | 97.4 | 60.1 | 87 | 99.02 |
| 26 | PEM | Lewatit | 37 | 5 | 4 | 55 | 97.67 | 69 | 82 | 99.09 |

Example 27

Pilot Plant

A reactor system containing 141 kilograms of A121 modified with PEM at a degree of neutralization of 37% using the above described method was rinsed with phenol until the water in the effluent was <1.0% as determined by Karl Fischer titration. The temperature of the feed was kept at about 49° C. The temperature of the effluent was about 74° C. The feed comprised phenol and 5.14% acetone. The overall space velocity was 2.2 WHSV. The effluent from the equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A commercial scale continuous process for the reaction of a ketone with a phenol to form a bisphenol comprising reacting a feed comprising a phenol and a ketone at a phenol to ketone mole ratio of about 4 to about 65 by passing the feed at a weight hour space velocity of about 0.1 to about 10 through a modified ion exchange resin catalyst at an initial temperature of about 30 to about 100° C. to produce an effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

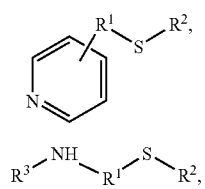

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing, and further wherein the effluent has a temperature about 4 to about 40° C. greater than the initial temperature.

2. The process of claim 1, wherein said ketone is acetone and said phenol is unsubstituted hydroxylbenzene.

3. The process of claim 1, wherein said ketone is present in amount of about 1.25 to about 8.5 weight %, based on the weight of the phenol.

4. The process of claim 3, wherein said ketone is present in an amount of about 2.5 to about 7.5% by weight, based on the weight of the phenol.

5. The process of claim 1, wherein said phenol comprises phenol, 2-cresol, 3-cresol, 2,6-dimethylphenol, resorcinol, napthol or mixtures of the foregoing phenols.

6. The process of claim 1, wherein said ketone comprises 9-fluorenone, benzophenone, acetone, acetophenone, cyclohexanone, 3,3,5-trimethylcyclohexanone, 4-hydroxyacetophenone, 4,4'-dihydroxybenzophenone or a mixture of the foregoing.

7. The process of claim 1, wherein said ketone comprises formaldehyde, acetaldehyde, propionaldehyde, butyraldehyde or a mixture of the foregoing.

8. The process of claim 1, wherein said weight hour space velocity is about 0.5 to about 8.

9. The process of claim 8, wherein said weight hour space velocity is about 0.6 to about 3.0.

10. The process of claim 1, wherein said initial temperature is about 40 to about 90° C.

11. The process of claim 10, wherein said initial temperature is about 45 to about 80° C.

12. The process of claim 1, wherein said premodification acidic milliequivalent per gram catalyst value is greater than or equal to about 4 when dry.

13. The process of claim 12, wherein said premodification acidic milliequivalent per gram catalyst value is greater than or equal to about 5 when dry.

14. The process of claim 1, wherein said degree of crosslinking is about 1.5% to about 6.0%.

15. The process of claim 14, wherein said resin is a mixture of resins of different degrees of crosslinking wherein the degree of crosslinking of each resin comprising the mixture is about 1.5 to about 6%.

16. The process of claim 1 wherein said degree of neutralization is about 35 to about 60 mole %.

17. The process of claim 1 wherein said phenol is a hydroxy aromatic compound with at least one unsubstituted position.

18. The process of claim 17 wherein said unsubstituted position is para to the hydroxy position.

19. The process of claim 17 wherein said phenol is substituted with at least one inert substituent.

20. The process of claim 1, wherein said mercapto promoter is cysteamine.

21. The process of claim 1, wherein said mercapto promoter is 4-pyridylethylmercaptan.

22. The process of claim 1, wherein said process has an average p/p selectivity greater than or equal to about 93%.

23. The process of claim 22, wherein said process has an average p/p selectivity greater than or equal to about 95%.

24. The process of claim 23, wherein said process has an average p/p selectivity greater than or equal to about 97%.

25. The process of claim 1, wherein said bisphenol resulting from the process has an average para-para:ortho-para ratio greater than 20.0.

26. The process of claim 25, wherein said bisphenol resulting from the process has an average para-para:ortho-para ratio greater than 30.0.

27. The process of claim 26, wherein said bisphenol resulting from the process has an average para-para:ortho-para ratio greater than 40.0.

28. The process of claim 1, wherein said process has an initial ketone conversion greater than or equal to about 90%.

29. The process of claim 28, wherein said process has an initial ketone conversion greater than or equal to about 95%.

30. The process of claim 29, wherein said process has an initial ketone conversion greater than or equal to about 97%.

31. The process of claim 1, wherein said process has a total bisphenol selectivity greater than or equal to about 98.5%.

32. The process of claim 1, wherein said ketone is added in a single portion.

33. The process of claim 1, wherein said ketone is added in multiple portions.

34. The process of claim 1, wherein the effluent has a temperature about 10 to about 30° C. greater than the initial temperature.

35. The process of claim 34, wherein the effluent has a temperature about 15 to about 25° C. greater than the initial temperature.

36. A commercial scale continuous process for the reaction of acetone with a phenol to form bisphenol A comprising reacting a feed comprising phenol and acetone at a phenol to acetone mole ratio of about 5 to about 40 by passing the feed at a weight hour space velocity of about 0.5 to about 3 through a modified ion exchange resin catalyst at an initial temperature of about 30 to about 80° C. to produce an effluent, wherein the acetone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 4%, the resin modified by neutralization of the acid sites with a mercapto promoter wherein the degree of neutralization is about 35 to about 45 mole % of the resin acid sites and the mercapto promoter is selected from the group consisting of promoter compounds I and II having the formula

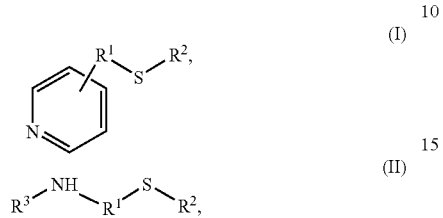

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing and further wherein the effluent has a temperature about 15 to about 25° C. greater than the initial temperature.

37. A process for the manufacture of polycarbonate comprising:

synthesizing a bisphenol by reacting a feed comprising a phenol and a ketone at a phenol to ketone mole ratio of about 4 to about 65 by passing the feed at a weight hour space velocity of about 0.1 to about 10 through a modified ion exchange resin catalyst at an initial temperature of about 30 to about 100° C. to produce effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

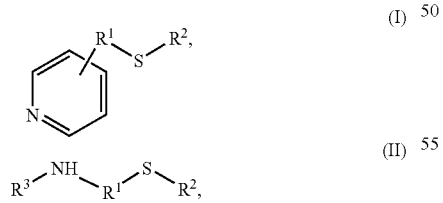

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing; and further wherein the effluent has a temperature about 4 to about 40° C. greater than the initial temperature;

and reacting said bisphenol with a carbonic acid derivative or a carbonate diester in the presence of a polymerization catalyst.

38. The process of claim 37, wherein the promoter is a promoter compound having the formula

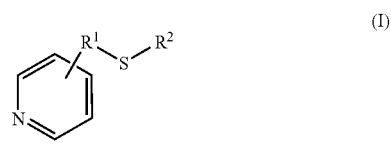

wherein $R^1$ is an alkylene having 1 to about 10 carbons and $R^2$ is a hydrogen, t-butyl or acyl.

39. A process for the manufacture of polycarbonate comprising:

synthesizing bisphenol A by reacting a feed comprising phenol and acetone at a phenol to acetone mole ratio of about 5 to about 40 by passing the feed at a weight hour space velocity of about 0.5 to about 3 through a modified ion exchange resin catalyst at an initial temperature of about 30 to about 80° C. to produce an effluent, wherein the acetone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 4%, the resin modified by neutralization of the acid sites with a mercapto promoter wherein the degree of neutralization is about 35 to about 45 mole % of the resin acid sites and the mercapto promoter is selected from the group consisting of promoter compounds I and II having the formula

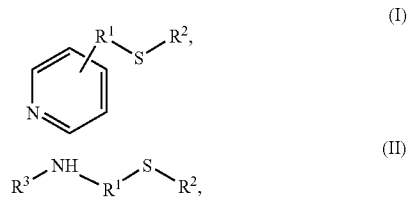

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing and further wherein the effluent has a temperature about 15 to about 25° C. greater than the initial temperature; and reacting said bisphenol A with a carbonic acid derivative or a carbonic diester in the presence of a polymerization catalyst.

40. The process of claim 39, wherein the promoter is a promoter compound having the formula

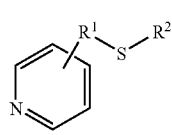

wherein $R^1$ is an alkylene having 1 to about 10 carbons and $R^2$ is a hydrogen, t-butyl or acyl.

41. A commercial scale continuous process for the reaction of a ketone with a phenol to form a bisphenol comprising reacting a feed comprising a phenol and a ketone at a phenol to ketone mole ratio of about 4 to about 65 by passing the feed at a weight hour space velocity of about 0.1 to about 10 through at least 150 kilograms of a modified ion exchange resin catalyst at an initial temperature of about 30 to about 100° C., wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

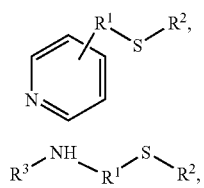

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing.

42. A commercial scale continuous process for the reaction of acetone with a phenol to form bisphenol A comprising reacting a feed comprising phenol and acetone at a phenol to acetone mole ratio of about 5 to about 40 by passing the feed at a weight hour space velocity of about 0.5 to about 3 through at least 150 kilograms of a modified ion exchange resin at an initial temperature of about 30 to about 80° C., wherein the acetone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 4%, the resin modified by neutralization of the acid sites with a mercapto promoter wherein the degree of neutralization is between about 35 and about 45 mole % of the resin acid sites and the mercapto promoter is selected from the group consisting of promoter compounds I and II having the formula

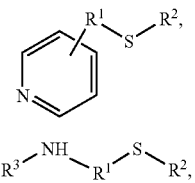

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing.

43. A process for the manufacture of polycarbonate comprising:
synthesizing a bisphenol by reacting a feed comprising a phenol and a ketone at a phenol to ketone mole ratio of about 4 to about 65 by passing the feed at a weight hour space velocity of about 0.1 to about 10 through at least 150 kilograms of a modified ion exchange resin catalyst at an initial temperature of about 30 to about 100° C., wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is selected from the group consisting of promoter compounds I and II having the formula

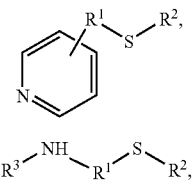

wherein $R^1$ is an alkylene having 1 to about 10 carbons, $R^2$ is a hydrogen, t-butyl or acyl and $R^3$ is hydrogen, $C_1$ to $C_5$ carboxylate or a branched, unbranched or cyclic alkyl group having 1 to about 10 carbons; derivatives thereof; and mixtures of the foregoing;
and reacting said bisphenol with a carbonic acid derivative or a carbonic diester in the presence of a polymerization catalyst.

44. The process of claim 42, wherein the promoter is a promoter compound having the formula

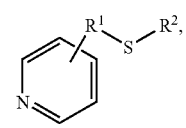

wherein R¹ is an alkylene having 1 to about 10 carbons and R² is a hydrogen, t-butyl or acyl.

45. A process for the manufacture of a polycarbonate comprising
synthesizing bisphenol A by reacting a feed comprising phenol and acetone at a phenol to acetone mole ratio of about 5 to about 40 by passing the feed at a weight hour space velocity of about 0.5 to about 3 through at least 150 kilograms of a modified exchange resin catalyst at an initial temperature of about 30 to about 80° C., wherein the acetone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 4%, the resin modified by neutralization of the acid sites with a mercapto promoter wherein the degree of neutralization is about 35 to about 45 mole % of the resin acid sites and the mercapto promoter is selected from the group consisting of promoter compounds I and II having the formula

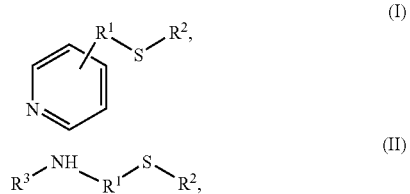

wherein R¹ is an alkylene having 1 to about 10 carbons, R² is a hydrogen, t-butyl or acyl and R³ is hydrogen, $C_1$ to $C_5$ carboxylate or a branched, unbranched or cyclic alkyl group having 1 to about 10 carbons; derivatives thereof; and mixtures of the foregoing; and
reacting said bisphenol A with a carbonic acid derivative or a carbonic diester in the presence of a polymerization catalyst.

46. The process of claim 45, wherein the promoter is a promoter compound having the formula

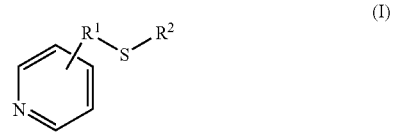

wherein R¹ is an alkylene having 1 to about 10 carbons and R² is a hydrogen, t-butyl or acyl.

47. A commercial scale continuous process for the reaction of a ketone with a phenol to form a bisphenol comprising reacting a feed comprising a phenol a ketone at a phenol to ketone mole ratio of about 4 to about 65 by passing thefeed at a weight hour space velocity of about 0.1 to about 10 through a modified ion exchange resin catalyst at an initial temperature of about 30 to about 100° C. to produce an effluent, wherein the ketone comprises less than 250 parts per million methanol and the modified ion exchange resin catalyst comprises a crosslinked gellular acid functionalized polystyrene resin having acid sites and a premodification acidic milliequivalent per gram catalyst value of greater than or equal to about 3.5 when dry and having a degree of crosslinking of about 1.5 to about 8%, the resin modified by neutralization of the acid sites with a mercapto promoter wherein the degree of neutralization is about 35 to about 75 mole % of the resin acid sites and the mercapto promoter is a promoter compound having the formula

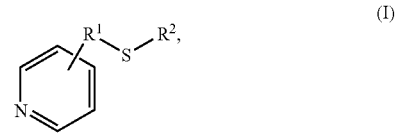

wherein R¹ is an alkylene having 1 to about 10 carbons and R² is a hydrogen, t-butyl or acyl and further wherein the effluent has a temperature about 4 to about 40° C. greater than the initial temperature.

48. The process of claim 47, wherein the effluent has a temperature about 10 to about 30° C. greater than the initial temperature.

49. The process of claim 47, wherein the effluent has a temperature about 15 to about 25° C. greater than the initial temperature.

50. The process of claim 47, wherein said ketone is acetone and said phenol is unsubstituted hydroxylbenzene.

51. The process of claim 47, wherein said ketone is present in amount of about 1.25 to about 8.5 weight %, based on the weigh to the phenol.

52. The process of claim 51, wherein said ketone is present in an amount of about 2.5 to about 7.5% by weight, based on the weight of the phenol.

53. The process of claim 47, wherein said phenol comprises phenol, 2-cresol, 3-cresol, 2,6-dimethylphenol, resorcinol, napthol or mixtures of the foregoing phenols.

54. The process of claim 47, wherein said ketone comprises 9-fluorenone, benzophenone, acetone, acetophenone, cyclohexanone, 3,3,5-trimethylcyclohexanone, 4-hydroxyacetophenone, 4,4'-dihydroxybenzophenone or a mixture of the foregoing.

55. The process of claim 47, wherein said ketone comprises formaldehyde, acetaldehyde, propionaldehyde, butyraldehyde or a mixture of the foregoing.

56. The process of claim 47, wherein said weight hour space velocity is about 0.5 to about 8.

57. The process of claim 56, wherein said weight hour space velocity is about 0.6 to about 3.0.

58. The process of claim 47, wherein said initial temperature is about 40 to about 90° C.

59. The process of claim 58, wherein said initial temperature is about 45 to about 80° C.

60. The process of claim 47, wherein said premodification acidic milliequivalent per gram catalyst value is greater than or equal to about 4 when dry.

61. The process of claim 60, wherein said premodification acidic milliequivalent per gram catalyst value is greater than or equal to about 5 when dry.

62. The process of claim 47, wherein said degree of crosslinking is about 1.5% to about 6.0%.

63. The process of claim 62, wherein said resin is a mixture of resins of different degrees of crosslinking wherein the degree of crosslinking of each resin comprising the mixture is about 1.5 to about 6%.

64. The process of claim 47, wherein said degree of neutralization is about 35 to about 60 mole %.

65. The process of claim 47, wherein said phenol is a hydroxy aromatic compound with at least one unsubstituted position.

66. The process of claim 65, wherein said unsubstituted position is para to the hydroxy position.

67. The process of claim 66, wherein said phenol is substituted with at least one inert substituent.

68. The process of claim 47, wherein said mercapto promoter is 4-Spyridylethylmercaptan.

69. The process of claim 47, wherein said process has an average p/p selectivity greater than or equal to about 93%.

70. The process of claim 69, wherein said process has an average p/p selectivity greater than or equal to about 95%.

71. The process of claim 70, wherein said process has an average p/p selectivity greater than or equal to about 97%.

72. The process of claim 47, wherein said bisphenol resulting from the process has an average para-para:ortho-para ratio greater than 20.0.

73. The process of claim 72, wherein said bisphenol resulting from the process has an average para-para:ortho-para ratio greater than 30.0.

74. The process of claim 73, wherein said bisphenol resulting from the process has an average para-para:ortho-para ratio greater than 40.0.

75. The process of claim 47, wherein said process has an initial ketone conversion greater than or equal to about 90%.

76. The process of claim 75, wherein said process has an initial ketone conversion greater than or equal to about 95%.

77. The process of claim 76, wherein said process has an initial ketone conversion greater than or equal to about 97%.

78. The process of claim 47, wherein said process has a total bisphenol selectivity greater than or equal to about 98.5%.

79. The process of claim 47, wherein said ketone is added in a single portion.

80. The process of claim 47, wherein said ketone is added in multiple portions.

* * * * *